United States Patent
Mills et al.

(10) Patent No.: US 6,383,169 B1
(45) Date of Patent: *May 7, 2002

(54) RELEASABLE WRAPPER FOR ABSORBENT ARTICLES SUCH AS SANITARY NAPKINS

(75) Inventors: Sue Ann Mills, Cincinnati; Bruce William Lavash, West Chester; Jeffrey Vincent Bamber, Cincinnati, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/867,034

(22) Filed: Jun. 2, 1997

Related U.S. Application Data

(62) Division of application No. 08/712,784, filed on Sep. 12, 1996, now Pat. No. 5,681,303, which is a continuation of application No. 08/380,769, filed on Jan. 30, 1995, now abandoned.

(51) Int. Cl.⁷ ................................................ A61F 13/15
(52) U.S. Cl. ........................ 604/385.02; 604/385.04; 604/385.05
(58) Field of Search ........................... 604/385.1, 386, 604/387, 389, 390, 385.01–385.05; 206/438, 440

(56) References Cited

U.S. PATENT DOCUMENTS

| | | | | |
|---|---|---|---|---|
| 5,413,568 A | * | 5/1995 | Roach et al. | 604/393 |
| 5,484,636 A | * | 1/1996 | Berg et al. | 604/390 |
| 5,569,228 A | * | 10/1996 | Byrd et al. | 604/387 |
| 5,569,230 A | * | 10/1996 | Fisher et al. | 604/387 |
| 5,683,377 A | * | 11/1997 | Mizutani | 604/390 |
| 5,792,131 A | * | 8/1998 | Mizutani | 604/390 |
| 5,800,654 A | | 9/1998 | Davis et al. | |
| 5,868,727 A | * | 2/1999 | Barr et al. | 604/387 |
| 5,954,201 A | * | 9/1999 | Finch et al. | 604/387 |

FOREIGN PATENT DOCUMENTS

| | | | | |
|---|---|---|---|---|
| JP | 5-9529 | | 2/1993 | |
| JP | 5506799 | * | 5/1993 | 604/387 |
| JP | 7039820 | * | 7/1995 | 604/387 |
| WO | WO 93/09743 A1 | | 5/1993 | |

* cited by examiner

Primary Examiner—John G. Weiss
Assistant Examiner—Jamisue Webb
(74) Attorney, Agent, or Firm—Matthew P. Fitzpatrick; Jeffrey V. Bamber; Kevin C. Johnson

(57) ABSTRACT

A releasable wrapper for absorbent articles such as sanitary napkins, panty liners, and adult incontinence devices, and the like which have side flaps is disclosed. The releasable wrapper covers the adhesive fasteners on the garment-facing side of the absorbent article and provides an individual package for the absorbent article.

8 Claims, 3 Drawing Sheets

RELEASABLE WRAPPER FOR ABSORBENT ARTICLES SUCH AS SANITARY NAPKINS

This is a division of application Ser. No. 08/712,784, filed on Sep. 12, 1996, which was a continuation of application Ser. No. 08/380,769, filed on Jan. 30, 1995 now abandoned.

FIELD OF THE INVENTION

The present invention relates to absorbent articles such as sanitary napkins, panty liners, adult incontinence devices, and the like which have side flaps. More particularly, the present invention concerns absorbent articles having side flaps that are provided with gathered portions that can expand to provide improved fit and coverage of the wearer's undergarment when the flaps are wrapped around the side edges of a wearer's undergarment.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearers panties in the crotch region and the wearer's thighs. Commonly, the flaps are provided with an attachment means for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, the flapped napkins commonly experience problems that keep them from being optimally effective. These problems generally result from the stresses exerted on the flaps when the sanitary napkins are worn.

When the flaps are folded down along the edges of the wearer's panties, stresses are created in the flaps, particularly when the flaps are relatively large in size. The stresses are especially high along the fold line at the edges of the wearer's panties where the flaps are bent from the body side of the panty to the underside of the panty. These stresses are caused by fitting a flap around the curved edges of a panty crotch. The stresses are magnified when a wearer sits or crouches because the edges of the panties are pulled outward against the flaps thus increasing the forces against this fold line. When the stresses become too high, the flaps may become detached from the panty and some portion of the aforementioned benefits of the flaps may be lost. In addition, even if the stresses are not sufficient to detach the flaps, they may still be sufficient to cause the flaps to bunch longitudinally inward. This effectively reduces the size of the flaps and the area of the wearer's undergarments that the flaps are able to cover. Thus, there is a commercial need for a way of eliminating or at least reducing the stresses that develop in the flaps when folded, so as to prevent them from becoming detached from the wearer's panties and losing ability to cover a given area of the panties.

A number of variations on the types of flaps described above have been presented in an attempt to solve these problems. A sanitary napkin having flaps with stress relief means in the form of a notch or a slit is described in U.S. Pat. No. 4,917,697 which issued to Osborn, III, et al. on Apr. 17, 1990. Absorbent articles having flaps and zones of differential extensibility for relieving the stresses which develop in the flaps are disclosed in U.S. Pat. No. 5,344,416 issued to Niihara on Sep. 6, 1994, and U.S. Pat. No. 5,354,400 issued to Lavash, et al. on Oct. 11, 1994. Although these sanitary napkins work quite well, the search for sanitary napkins having improved flaps has continued.

Therefore, it is an object of the present invention to provide an absorbent article, such as a sanitary napkin, having flaps that provides the absorbent article with further improved means for relieving the stresses that develop in the flaps when they are folded down along the edges of the crotch of the wearer's undergarments and affixed to the underside of the undergarments. It is another object of the present invention to provide such an absorbent article with flaps that do not lose their ability to cover a given area of the wearer's undergarments during wear.

These and other objects of the present invention will be more readily apparent when considered in reference to the following description and when taken in conjunction with the accompanying drawings.

SUMMARY OF THE PRESENT INVENTION

The present invention is directed to an absorbent article, such as a sanitary napkin, having flaps that are provided with gathered portions that can expand to relieve the stresses that develop in the flaps when the flaps are folded down around the edges of the crotch of the wearer's undergarments.

The absorbent article comprises a main body portion having two spaced apart longitudinal edges and two spaced apart transverse edges, and a pair of flaps associated with said main body portion, one extending laterally outward beyond each longitudinal edge of the main body portion. The main body portion comprises a liquid pervious topsheet, a liquid impervious backsheet joined to the topsheet, and an absorbent core positioned between the topsheet and the backsheet. The main body portion has a first end region, a second end region, and a central region disposed between the first and second end regions. The absorbent article has a principal longitudinal centerline and a principal traverse centerline. The flaps have a proximal edge, a distal edge, and a flap transverse centerline that intersects the principal longitudinal centerline of the absorbent article.

The absorbent article is provided with a gathered portion positioned between the principal longitudinal centerline and the distal edge of the flaps. A restraint, which extends along at least part of the central region of the main body portion, restrains portions of the gathered portion from unfolding while allowing the ends of the gathered portion to unfold at locations disposed longitudinally away from said flap transverse centerline. In particularly preferred embodiments, the sanitary napkin also comprises one or more zones of differential extensibility. The zones of differential extensibility comprise material that has a greater range of extensibility outward than the points on the flaps that are located along the flap transverse centerline. The zones of differential extensibility are preferably disposed laterally outward from the gathered portions and longitudinally away from the flap transverse centerline. A novel releasable wrapper is also provided for enclosing and protecting the sanitary napkin prior to use.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
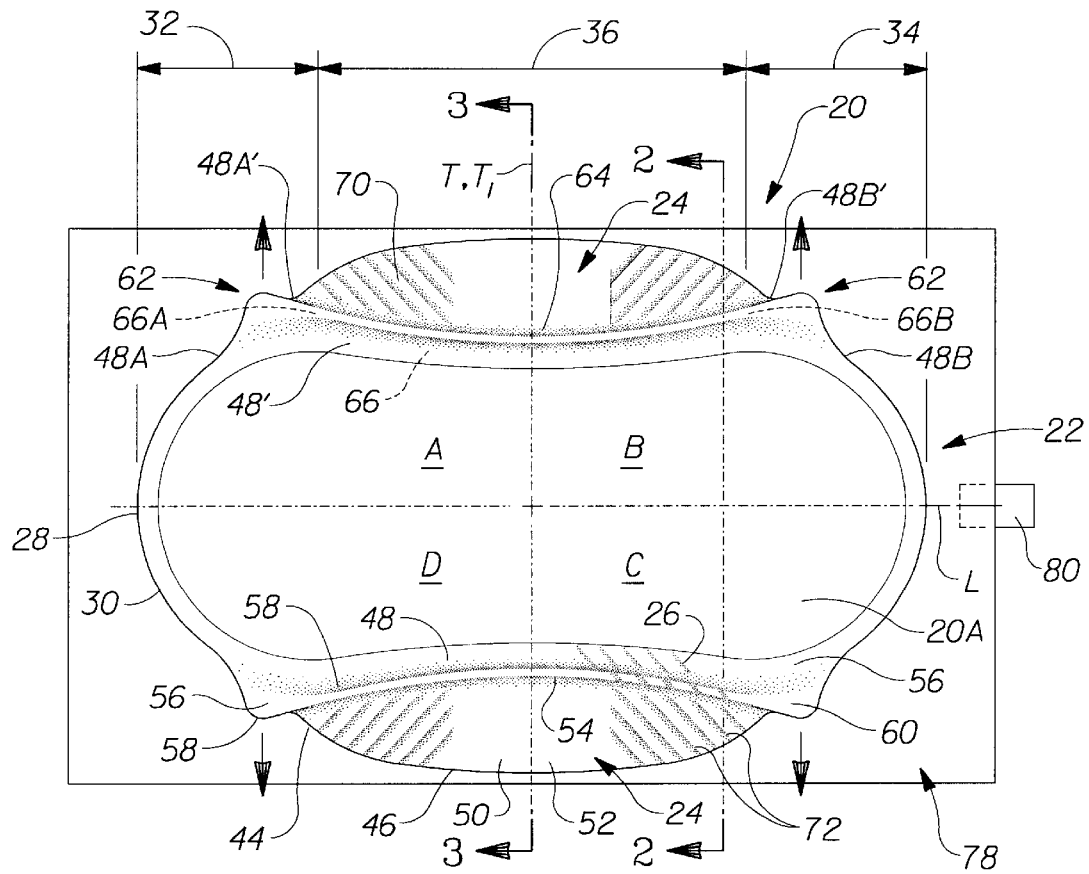
FIG. 1 is a top plan view of a preferred sanitary napkin of the present invention.
Figure 2:
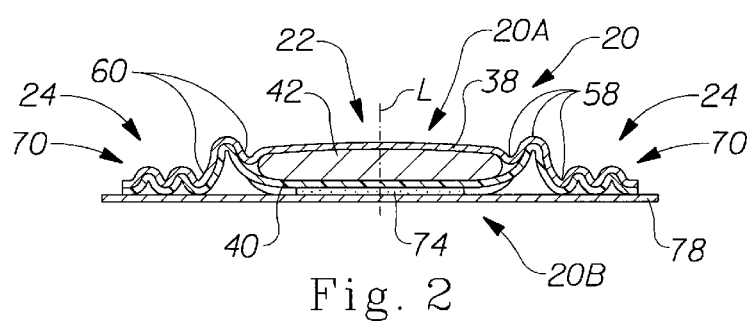
FIG. 2 is a cross-sectional view taken along line 2—2 of FIG. 1 through the portions of the flaps which can expand when the sanitary napkin is wrapped around the edge of a wearer's panty.
Figure 3:
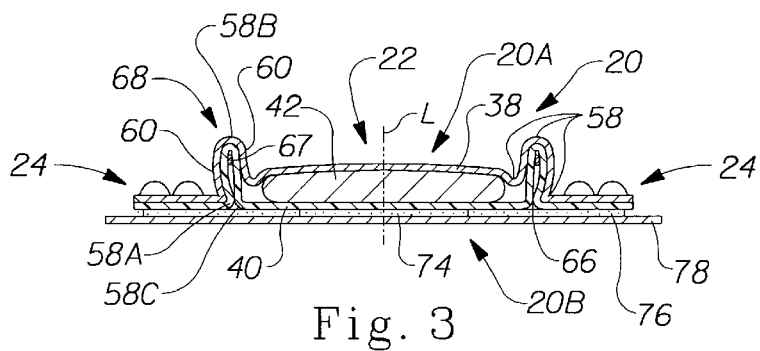
FIG. 3 is a cross-sectional view taken along line 3—3 of FIG. 1 which passes through the flap transverse centerline.

FIGS. 1–3 show one preferred embodiment of a disposable absorbent article of the present invention, sanitary napkin 20. As shown in FIG. 1, the sanitary napkin 20 basically comprises a main body portion 22 and two flaps 24. (In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.)

The sanitary napkin 20 (and the main body portion thereof) has two surfaces, a liquid pervious body-contacting surface or "body surface" 20A that is intended to be worn adjacent to the body of the wearer and a liquid impervious garment surface 20B. The sanitary napkin 20 is shown in FIG. 1 as viewed from its body surface 20A. The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion of the sanitary napkin 20. The main body portion 22 also has two end regions, which are designated first end region 32 and second end region 34. A central region 36 is disposed between the end regions 32 and 34. The end regions 32 and 34 extend outwardly from the edges of the central region 36 about ⅛ to about ⅓ of the length of the main body portion. A detailed description of a sanitary napkin having such a central region 36 and the two end regions 32 and 34 is contained in U.S. Pat. No. 4,690,680 issued to Higgins on Sep. 1, 1987, the disclosure of which is incorporated herein by reference.

The main body portion of the sanitary napkin 20 can be of any thickness, including relatively thick, relatively thin, or even very thin. The embodiment of the sanitary napkin 20 shown in FIGS. 1–3 of the drawings is intended to be an example of a moderately thick sanitary napkin having a main body portion similar to that described in U.S. Pat. Nos. 5,234,422 and 5,308,346 issued to Sneller, et al., the disclosures of which are incorporated herein by reference. It should be understood that the sanitary napkin shown is merely one preferred embodiment, and that the present invention is not limited to absorbent articles of the type or having the specific configurations shown in the drawings. For example, the main body portion 22 of the sanitary napkin can also be embossed with channels such as those described in the Sneller patents.

FIG. 2 shows the individual components of the main body portion 22 of the sanitary napkin 20 of the present invention. The main body portion 22 generally comprises at least three primary components. These include a liquid pervious topsheet 38, a liquid impervious backsheet 40, and an absorbent core 42 positioned between the topsheet 38 and the backsheet 40. Suitable materials for these components of the sanitary napkin 20 are described in greater detail in the patent publications which are incorporated by reference herein. The topsheet, the backsheet, and the absorbent core may be assembled in a variety of configurations known in the art (including so called "sandwich" products and "tube" products).

Several preferred sanitary napkin configurations are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. Nos. 4,950,264 and 5,009,653, both entitled "Thin, Flexible Sanitary Napkin" issued to Osborn on Aug. 21, 1990 and Apr. 23, 1991, respectively; the aforementioned patent applications issued to Sneller, et al.; U.S. patent application Ser. No. 08/096,121 entitled "Absorbent Articles Having Panty Covering Components That Naturally Wrap the Sides of Panties" filed Jul. 22, 1993, in the name of Lavash, et al. (PCT Publication No. WO 94/02096, published Feb. 3, 1994); and U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. The main body portion 22 of the sanitary napkin may also be comprised of one or more extensible components such as those sanitary napkins, and the like described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993). The disclosures of all of the preceding publications are incorporated by reference herein.

The sanitary napkin 20, as shown in FIG. 2, is assembled in a sandwich construction in which the topsheet 38 and the backsheet 40 have length and width dimensions generally larger than those of the absorbent core 42. The topsheet 38 and the backsheet 40 extend beyond the edges of the absorbent core 42 and are joined together along a seam to form at least portions of the periphery 30 of the main body portion. The seam can be formed by any means commonly used in the art for this purpose, such as gluing, crimping, or fusing. It is to be understood that the embodiment illustrated is only one possible embodiment, albeit a preferred one. Other possible embodiments include one in which an absorbent core 44 is essentially completely wrapped with topsheet before it is placed on a backsheet. The main body portion 22 can also comprise an absorbent core which possesses sufficient integrity to stand alone and is liquid pervious on one surface while the other surface has been treated to render it liquid impervious.

The sanitary napkin 20 of the present invention comprises a pair of flaps 24 joined to the main body portion 22. The flaps 24 extend from their proximal edges 44 laterally outward beyond the longitudinal side edges 26 of the main body portion 22 to their distal edges 46. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The flaps 24 of the one preferred embodiment shown in FIGS. 1–3 are integral with the main body portion 22 of the sanitary napkin. In such a case, the topsheet 38 may form the body-facing surface of both the flaps 24 and the main body portion 22, and the backsheet 40 may form the garment-facing surface of the same. It is possible for the absorbent material of the sanitary napkin 20 to extend into the flaps 24 to form a flap absorbent core, as described in greater detail in U.S. Pat. No. 4,917,697 (although the embodiment shown in FIGS. 1–3 does not utilize such a construction). In alternative embodiments, the flaps 24 may be comprised of separate pieces of material or elements which are attached to the main body portion 22. When the flaps comprise separate elements, they can be joined to the main body portion 22 by any techniques known to those skilled in the art. Such techniques include, but are not limited to adhesives, heat and/or pressure, ultrasonics, etc.

The flaps 24, whether they are integral with the main body portion or separate elements attached thereto, are each associated with main body portion 22 along a juncture. This is typically a longitudinally-oriented (or "longitudinal") juncture, such as line of juncture 48. As used herein, the terms "juncture" (or "line of juncture") refer to regions where the flaps 24 extend from or are joined to the main body portion 22. The junctures can be any of various curved or straight lines, but they are not limited to lines. Thus, the junctures can comprise regions, flanges, strips, intermittent lines, and the like. In the sanitary napkin 20 illustrated in FIG. 1, line of juncture 48 is a generally longitudinally oriented region that can range from being relatively straight to slightly concave. When the flaps 24 are integral with the main body portion 22, the lines of juncture 30 may represent lines of demarcation between the main body portion 22 and the flaps 24, although it is not necessary that there be a precise line of demarcation. Thus, it is also possible to either consider the line designated 48' in FIG. 1 as a line of juncture (in which case the flaps 24 are indirectly joined to the main body portion through folded regions 60), or for the line of juncture to be considered to be located between lines 48 and 48'.

It is also not necessary that the flaps 24 extend from (or be joined along) the longitudinal edges 26 of the main body portion 22. The flaps 24 can, for instance, be joined to the main body portion 22 any distance inward (or "inboard") from the longitudinal edges 26 toward the principal longitudinal centerline L. From the foregoing, it is apparent that the flaps 24 can each be joined to the main body portion 22 along the longitudinal edges 26 of the main body portion 22, or along the principal longitudinal centerline L, or at any place between the principal longitudinal centerline L and the longitudinal edges 26 of the main body portion 22.

The flaps 24 have a proximal edge 44 at or adjacent the time of juncture 48. A distal edge (or "free end") 46 is remote from the line of juncture 48. As shown in FIG. 1, each flap 24 is divided into a front half 50, and a back half 52 by a flap transverse centerline $T_1$. The flap transverse centerline $T_1$ may coincide with the principal traverse centerline T of the sanitary napkin, but this is not absolutely required. In other embodiments, the flap transverse centerline $T_1$ may be offset either to the front or to the rear of the principal transverse centerline T. The flap transverse centerline $T_1$ extends through the principal longitudinal centerline 1 to divide the sanitary napkin into four quarters A, B, C, and D.

FIGS. 1–3 show that the flaps 24 preferably each have at least one gathered portion 54. The term "gathered portion" refers to a portion of the sanitary napkin which is gathered inward, preferably toward the principal longitudinal centerline L of the sanitary napkin. The gathered portion also preferably remains in a gathered condition during the time the sanitary napkin is worn. The gathered portion 54 can be formed entirely in the flaps 24, entirely in the main body portion 22, or partially in the flaps 24 and partially in the main body portion 22. Preferably, the sanitary napkin 20 has two gathered portions 54, one adjacent each flap 24.

The gathered portions 54, as shown in FIGS. 1–3, are preferably located in the regions surrounding and including the junctures 48 of the flaps 24 with the main body portion 22. FIG. 1 shows that the flaps 24 also have portions which are not gathered inward to the same extent as the gathered portions 54. The portions of the flaps 24 that are disposed longitudinally away from the gathered portions are referred to herein as "expandable portions" 56. The expandable portions 56 should be capable of expanding (preferably generally in the transverse direction (as shown by the arrows in FIG. 1)) when the flaps 24 are folded around the edges of the wearer's panties.

The gathered portions 54 and the expandable portions 56 can be formed in any suitable manner. In the preferred embodiment shown in FIGS. 1–3, the gathered portions 54 are formed by pleating or folding the flaps 24 with generally longitudinally-oriented fold lines 58 to form folded or pleated sections (or "pleats") 60. The fold lines 58 can run along and/or inboard or outboard of the juncture 48 of the flaps and the main body portion 22. The folded actions 60 of the flaps 24 are preferably folded and arranged side-by-side. The folding of the flaps 24 creates an enclosed tube or casing which is left open at its ends. In alternative embodiments in which it is not desired to have the folded sections stand up, the folded sections 60 may be folded on top of each other (that is, stacked perpendicular to the plane of the sanitary napkin). The folded sections 60 preferably run the length of the juncture 48. The folded sections 60 are gathered in and restrained from opening by a restraint, such as a fold or pleat restraint 66 that preferably extends the length of the entire central region 36 of the main body portion 22, but does not extend into the end regions 32 and 34. This provides the sanitary napkin 20, and particularly the flaps 24, with expandable end portions 56 which are generally extensible in the transverse direction and with center portions (along the central region 36 of the main body portion 22) which are not transversely extensible.

In such a folded embodiment, the folded sections 60 of the sanitary napkin can be provided with any number of fold lines. For instance, in the most basic form of the folded embodiment, the flaps 24 can simply be folded inward toward the principal longitudinal centerline L at a single line along the juncture 48 and tacked to the main body portion 22 in the region of the juncture 48. Typically, however, as shown in FIGS. 1–3, the sanitary napkin will have at least three fold lines 58, which are designated 58A, 58B, and 58C. Fold lines 58A and 58C will be referred to as the outer fold lines, and fold line 58B is referred to as the center fold line. The folded portions 60 of the sanitary napkin are preferably arranged so that the center fold line 58B is approximately evenly spaced between the outer fold lines 58A and 58C. The folded portions 60 of the sanitary napkin are preferably restrained so that the outer fold lines 58A and 58C are both joined to the side of the main body portion 22 as shown in FIG. 3 in approximately the same plane as the bottom of the backsheet of the sanitary napkin. The fold lines 58 are preferably spaced so that the folded portions 60 between the outer fold lines 58A and 58C and the center fold line 58B extend vertically upward above the plane defined by the topsheet of the sanitary napkin to form a pair of double wall barriers (or "barrier leg cuffs") 68 along the longitudinal edges 26 of the main body portion 22 of the sanitary napkin. The restraint 66 should preferably extend substantially the entire length of the central portion 36 of the main body portion in order to form these barriers 68.

The restraint 66 can be any suitable type of element that is capable of keeping a portion of the folded material from unfolding. Suitable restraints 66 include, but are not limited to adhesives, ultrasonic bonds, heat and/or pressure bonds, tapes, etc. These different types of restraints can be in an unlimited number of configurations. Such configurations can include spots, lines, patches, etc. The ends 66A and 66B of the restraint 66 are preferably spaced equal distance away from the flap transverse centerline $T_1$. This creates flaps with expandable portions 56 which are able to open up an equal amount in both the front and back halves 50 and 52. In alternative embodiments, however, it may be desirable for the restraint 66 to be offset more toward one end of the sanitary napkin than the other to adapt the sanitary napkin to fit various types of panties.

The sanitary napkin can have two restraints 66, one for each flap, or it can have a single restraint that spans from one flap to the other. In alternative embodiments, the sanitary napkin could have more than one restraint 66 for each flap 24. In the preferred embodiment shown in FIGS. 1–3, the sanitary napkin has one restraint 66 for each flap. The restraint 66 shown in FIGS. 1–3 is an "interior" restraint (i.e., it is located in between two folded sections 60 of the flaps 24). In alternative embodiments, the restraint 66 can be of a type which secures the folded sections 60 of the flaps 24 from the outside (or exterior) of the folded sections 60. The restraint 66 may be of any size provided it is no larger than the length of the juncture 48. This allows the expandable portions 56 of the flaps 24 to open properly. This is the case since the expandable portions 56 of the flaps 24 will typically open from the ends 48A and 48B of the lines of juncture 48 to the ends 66A and 66B of the restraint 66.

The sanitary napkin 20 can also be provided with an optional means for elastically contracting the double-wall barrier 68, such as elastic strand 67 inside each of the folded portions 60. The elastic strands 67 can be used to assist the stand-up barriers in staying upright so that they form a tight seal against the wearer's body to prevent leakage of exudates. One suitable construction for an elasticized stand-up barrier is described in U.S. Pat. No. 4,909,803 issued to Aziz on Mar. 20, 1990.

The sanitary napkin 20 preferably also has at least one zone of differential extensibility (or "zone of extensibility") 70. The term "zone of differential extensibility", as used herein, refers to a portion of the sanitary napkin 20 which is capable of extending a differing amount (preferably a greater amount), than surrounding portions of the sanitary napkin 20. Preferably, as shown in FIG. 1, the sanitary napkin 20 has four zones of differential extensibility 70, one in each quarter of the sanitary napkin 20. The zones of differential extensibility 70 act to further relieve the stresses which develop in the flaps 24 when they are folded around the sides of the wearer's panty crotch.

The zones of differential extensibility 70 are preferably primarily extensible in a greater amount generally outward in the transverse direction. This is generally in the direction of the arrows shown in FIG. 1. As used herein, the phrase "generally in the transverse direction" means that the extensibility has a transverse component. All of the extension, however, need not be exactly parallel to the principal transverse centerline, T, of the sanitary napkin. For example, in the embodiment shown in FIG. 1, the zones of differential extensibility 70 are extensible in a direction between the longitudinal and transverse directions. The extensibility of the zones of differential extensibility 70, however, is preferably oriented more in the transverse direction than in the longitudinal direction so that it is still generally in the transverse direction. Although, it is also possible that in other embodiments, the extensibility of the zones of differential extensibility can be oriented more in the longitudinal direction than the transverse direction, or even entirely in the longitudinal direction.

The zone(s) of differential extensibility 70 can comprise any structure capable of extending a greater amount in the transverse direction than the surrounding portions of the sanitary napkin. Suitable structures for the zones of differential extensibility 70 include, but are not limited to zones of material that are mechanically strained, corrugated, "ring rolled", folded, "SELFed" (as described in U.S. patent application Ser. No. 08/124,180 filed by Mansfield, et al.), pleated, or joined along a curved juncture. These structures (although shown in FIGS. 1–3 as only being part of the flaps 24), can comprise portions of the main body portion 22, portions of the flaps 24, or both. Examples of sanitary napkins with zones of differential extensibility are further described in the aforementioned U.S. Pat. No. 5,354,400 issued to Lavash, et al. on Oct. 11, 1994, and U.S. Pat. No.

5,389,094 to be issued to Lavash, et al. on Feb. 14, 1995, the disclosures of both of which are incorporated by reference herein.

The sanitary napkin 20 shown in FIGS. 1–3 has flaps with corner regions 62 that have been provided with differential extensibility by ring rolling the corner regions. The corner regions are ring rolled in accordance with methods described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992. The ring rolling (or pre-corrugating) should be applied so that the fold fines 72 in the corrugations are oriented generally in the longitudinal direction. The phrase "generally in the longitudinal direction" (and similar phrases), as used herein, means oriented more in the longitudinal dimension than in the transverse dimension. Thus, the fold lines 72 may angle away from the principal longitudinal centerline L. In the preferred embodiment shown in FIGS. 1–3, the fold lines 72 form an angle of between about 40°–45° with the principal longitudinal centerline L. This will provide the desired transverse direction extensibility.

The zones of differential extensibility 70 are generally located laterally outboard of the gathered portions 54 and expandable portions 56 of the sanitary napkin in the embodiment shown in FIGS. 1–3. The zones of differential extensibility 70 are also preferably located in the corner regions 62 of the sanitary napkin 20. The sanitary napkin 20 has four corner regions 62 (two corner regions either in and/or by each flap, and one in each quarter). The term "corner regions" 62, as used herein, refers to portions of the sanitary napkin 20 that are generally located along or adjacent a portion of the juncture 48 of the flaps 24 with the main body portion 22. The corner regions 62 for each flap 24 are located in two areas in the regions of the ends 48A and 48B (or 48A' and 48B) of each juncture 48 (or 48'). One corner region 62 is located adjacent the longitudinal juncture 48 in the front half 50 of the flap 24. The other is adjacent the longitudinal juncture 48 in the back half 52 of the flap 24. The corner regions 62 are preferably at least partially disposed longitudinally away from the flap transverse centerline $T_1$ in each direction. (Thus, the corner regions 62 may be described as being longitudinally "remote" from the flap transverse centerline $T_1$.)

In the most preferred case (as will be subsequently described in greater detail), the zones of differential extensibility 70 are located along a portion of the fold line where the flaps 24 are folded around the wearer's panty crotch. The fold line will typically be located along or adjacent the longitudinal juncture 48 of each flap 24. Since the terms "portions", "zones", and "regions", as used herein, refer to general areas, the zones of differential extensibility 70 and the corner regions 62 are, thus, not limited to points which lie precisely on the lines of juncture 48. Typically, they will include both those points which lie on the lines of juncture 48 as well as the surrounding areas of the sanitary napkin 20 (which include the aforementioned fold lines). The longitudinal junctures, thus, may merely serve as approximations for the location of the zones of differential extensibility 70.

In alternative embodiments, the zones of differential extensibility 70 need not be located laterally outboard of the gathered portions 54 and the expandable portions 56, It is also possible for the zones of differential extensibility 70 to be at least located laterally inward of the expandable portions 56, or even at least pad within the boundaries of the expandable portions 56. The location of a zone of differential extensibility 70, or a portions thereof within the boundaries of the expandable portions 56 can be advantageously used to further increase the amount of extension provided by the zone of differential extensibility. Any of these types of arrangements can be beneficial provided the operation of each of the different types of structures do not unduly interfere with the other.

Figure 4:
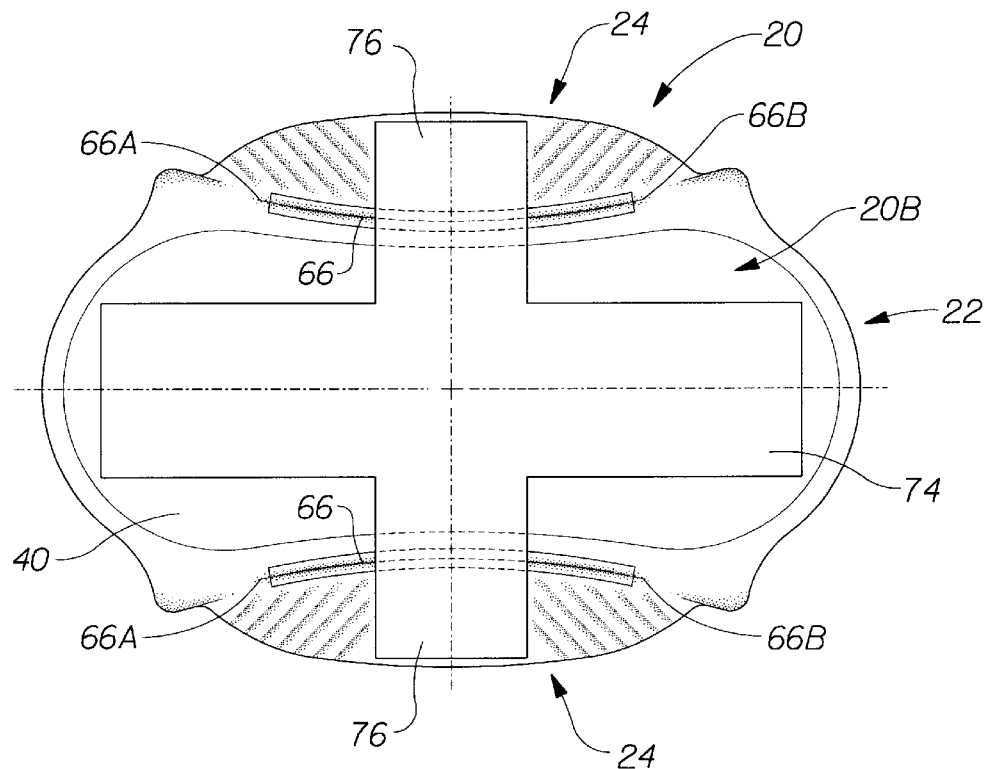
FIG. 4 is a bottom plan view of the sanitary napkin shown in FIG. 1, with the releasable wrapper removed.

The sanitary napkin 20 preferably also has fasteners that are adapted to secure the sanitary napkin 20 to the crotch region of an undergarment. FIGS. 2, 3, and 4 show one preferred type of fastener, adhesive attachment means, such is central pad adhesive 74 and flap adhesive 76. The fasteners used with the sanitary napkin of the present invention are, however, not limited to adhesive attachment means. Any type of fastener used in the art can be used for such purpose. For example, the sanitary napkin 20 could be secured to the wearer's undergarment by mechanical fasteners, or a combination of adhesive and mechanical fasteners. For simplicity, however, the fasteners will be described in terms of adhesive attachment means and are preferably pressure sensitive adhesive fasteners. Suitable pressure sensitive adhesive fasteners are described in greater detail in U.S. Pat. No. 4,917,697.

The adhesive fasteners can be arranged in any suitable configuration. In the preferred embodiment shown, the central pad adhesive 74 and flap adhesive 76 form one continuous adhesive patch that is in the shape of a cross. The central pad adhesive 74 provides an adhesive attachment means for securing main body portion 22 in the crotch portion of a panty. The flap adhesive 76 portion of the adhesive pattern is used to assist in maintaining the flaps 24 in position after they are wrapped around the edges of the crotch portion of the panty. The flaps 24 can be maintained in position by attaching the flaps 24 to the undergarment, or to the opposing flap. The fact that there are no gaps between the central pad adhesive 74 and the flap adhesive 76 has the effect of holding the sanitary napkin in place better and reducing any tendency for the main body portion 22 to bunch transversely inward and make the flaps 24 come unattached from the wearer's panty.

The central pad adhesive 74 and the flap adhesives 76 may each be covered by separate removable release liners to keep the adhesives from sticking to extraneous surfaces prior to use. Preferably, however, the adhesive attachment means are both covered by a single release liner (or "releasable wrapper") 78. Even more preferably, the release liner 78 also serves as an individual package for the sanitary napkin. Suitable release liners that also serve as an individual package for a sanitary napkin are described in U.S. Pat. No. 4,556,146 issued to Swanson, et al. (which discloses a tri-folded sanitary napkin and wrapper) and in U.S. patent application Ser. No. 08/247,912 filed May 23, 1994, which was originally filed Jun. 5, 1990 (PCT Publication No. WO 91/18574, published Dec. 12, 1991).

Figure 3A:
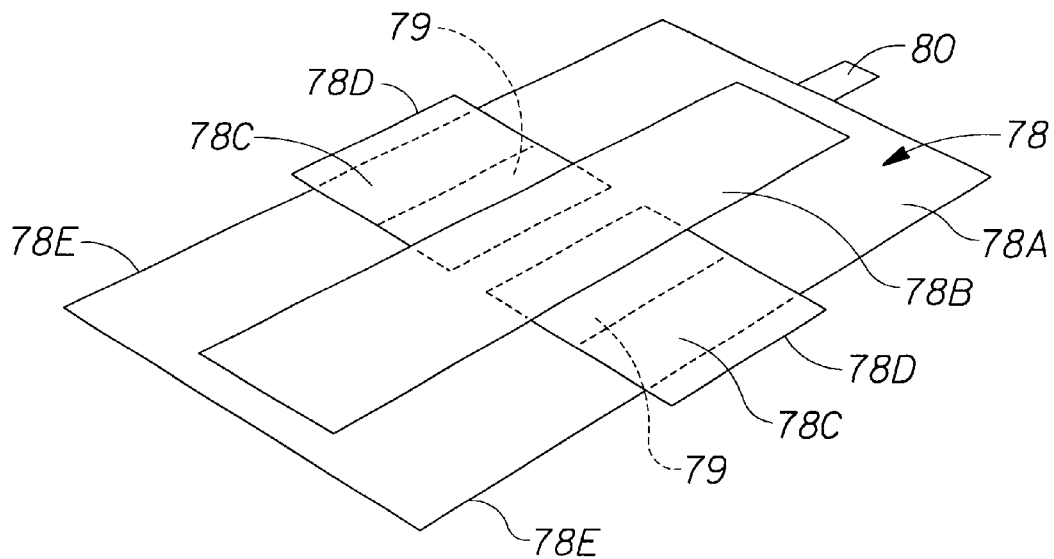
FIG. 3A is a perspective view of one particularly preferred releasable wrapper prior to the placement of the same on the sanitary napkin.

FIG. 3A shows an especially preferred version of a releasable wrapper 78 for use with the sanitary napkin 20 of the present invention. As shown in FIG. 3A, the releasable wrapper, generally designated by reference number 78 comprises several components. These include: a main wrapping sheet 78A; an optional release component, such as a release paper or release coating 78B; and, a pair of flap release elements 78C.

The main wrapping sheet 78A can comprise any material known in the art as being suitable for use as a releasable wrapper material. It may have a release coating thereon (that is, on its inside surface) so that it can be releasably attached to the central pad adhesive 74. Alternatively, the main wrapping sheet 78A may have a release paper adhered to its inside surface as shown in FIG. 3A, and the central pad adhesive 74 is adhered to the release paper rather than directly to the main wrapping sheet 78A. The flap release elements 78C are joined to the main wrapping sheet 78A such as by flap release element securement means 79. The flap release elements 78C are positioned so that they will underlie the flap adhesives 76 when the main body portion 22 is placed on the main wrapping sheet 78A It should be understood that, although the flap release elements 78C are shown as comprising two separate elements, it is also possible that the flap release elements 78C can comprise a single element or strip of material that has two portions, one at each of its ends which comprise the flap release elements. The flap release elements 78C are preferably pivotally connected to the main wrapping sheet 78A.

Figure 3B:
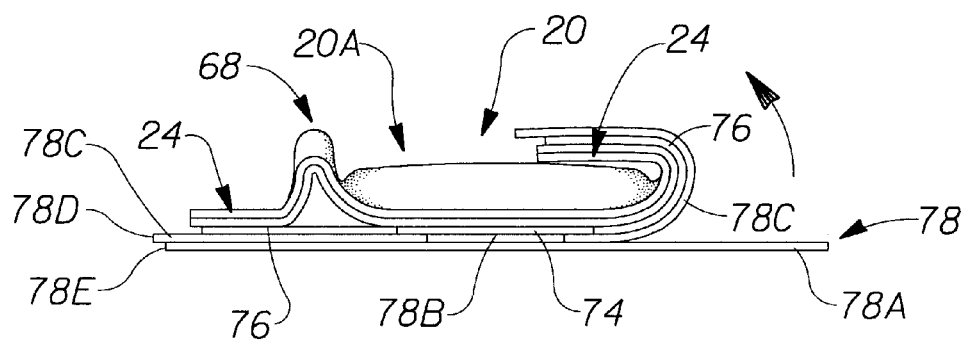
FIG. 3B is an end view of the sanitary napkin shown in FIGS. 1–3, which shows the folding of one of the flaps of the sanitary napkin into position before enclosing the same within the particularly preferred type of releasable wrapper.

The key to the functioning of this preferred releasable wrapper 78 is that the end portions comprising the release elements 78C cover the flap adhesive 76 and are able to pivot relative to the main wrapping sheet 78A as shown in FIG. 3B. The pivoting enables the flaps 24 to be folded over the body surface 20A of the sanitary napkin. This allows the flaps 24A to be folded so that the resulting package is smaller and more convenient for the user to carry than if the releasable wrapper were folded around the sanitary napkin with the flaps extended as shown in FIG. 1.

The sanitary napkin 20 is prepared for packaging when the sanitary napkin and its flaps 24 are placed flat on the releasable wrapper 78 as shown in FIG. 1. The flaps 24 and the releasably attached flap release elements 78C covering the flap adhesives 76 are folded over the body surface 20A of the sanitary napkin The flaps 24 can be retained in this body surface-facing relationship (or topsheet-facing relationship) in a number of different ways. One way to maintain the flaps 24 folded over the topsheet is by placing a spot of adhesive between the flaps 24 and the body surface 20A of the sanitary napkin. Preferably, however, the flaps 24 are temporarily maintained in a topsheet-facing relationship by placing a folding bar on top of the flaps during the packaging process, and then tri-folding the main body portion 22 of the sanitary napkin 20 and wrapper 78 about transverse axes with the flaps 24 folded so that the tri-folding of the main body portion 22 around the flaps 24 holds the flaps in place. In such a configuration, the advantage of the releasable wrapper 78 is that when the releasable wrapper 78 is unfolded from a tri-folded configuration, the sanitary napkin 20 can be conveniently removed from the releasable wrapper 78 in a one-piece motion. The user can, for example, hold one end of the releasable wrapper 78 with one hand and then grasp the end of the sanitary napkin 20 which is adjacent thereto with the other hand, and simply peel the sanitary napkin 20 from the wrapper 78.

While a preferred sanitary napkin embodiment has been described, numerous other sanitary napkin embodiments having flaps are available and are disclosed in the literature. These could be provided with the gathered portions of the present invention. In particular, sanitary napkins having flaps are disclosed in U.S. Pat. No. 5,346,486 entitled "Sanitary Napkin Having Laterally Extensible Means for Attachment to the Undergarment of the Wearer", issued Sep. 13, 1994, in the name of Osbom, et al., U.S. Pat. Nos. 5,009,653 and 4,950,264, both entitled "Thin Flexible Sanitary Napkin" which issued to Osborn on Apr. 23, 1991 and Aug. 21, 1990, respectively, U.S. Pat. No. 4,917,697 entitled "Sanitary Napkin Having Flaps and Stress Relief Means" which issued to Osbom, III, et al. on Apr. 17, 1990, U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957. Suitable absorbent articles in the form of pantiliners that could be provided with such flaps are disclosed in U.S. Pat. No. 4,738,676 entitled "Pantiliner" issued to Osborn on Apr. 19, 1988. Suitable absorbent articles, at least some of which are in the form of adult incontinence products, are described in U.S. Pat. Nos. 5,300,054 issued to Feist, et al. on Apr. 5, 1994, and 5,304,161 issued to Noel, et al. on Apr. 19, 1994.

In addition, in one particularly preferred version of the sanitary napkin of the present invention, the flaps 24 can be provided with two double-wall barriers along each side of the napkin. One of these double-wall barriers (preferably the interior barrier) is constructed as described herein, and the other double-wall barrier is provided as described in U.S. Pat. No. 4,589,876 issued to Van Tilburg. Having now described some sanitary napkins that can be provided with gathered portions, the sanitary napkin of the present invention will now be described in greater detail with relation to the function of the same in the wearer's undergarments.

Figure 5:
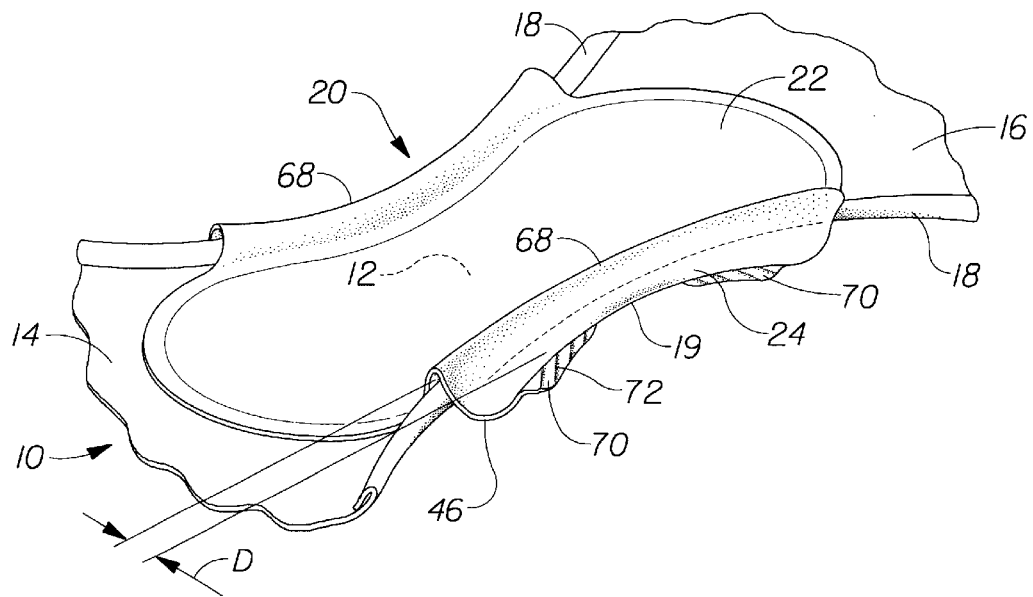
FIG. 5 is a perspective view of the sanitary napkin shown in FIGS. 1, 2, 3, and 4 in an in-use configuration.

FIG. 5 is a depiction of the sanitary napkin 20 of the present invention in place in an undergarment of the type commonly worn by many women and well known as a panty 10. The configuration of the sanitary napkin 20 shown in FIG. 5 is presented primarily for purposes of discussion, rather than to limit the possible configurations the sanitary napkin may take in use. It should be understood that the sanitary napkin of the present invention may also take other configurations in use.

The panty 10 comprises a crotch portion 12, a front section 14, and a back section 16. The crotch portion 12 joins the front and back sections and comprises two elasticized side edges 18. The sanitary napkin 20 is utilized by removing the releasable wrapper 78 and placing the sanitary napkin 20 in the panty 10 as shown in FIG. 5. The center of main body portion 22 is placed in the crotch portion 12 of the panty 10 with the backsheet 40 in contact with the inner surface of crotch portion 12 of the panty and one end of main body portion 22 extending towards the front section 14 of the panty and the other end towards the back section 16. Central pad adhesive 74 maintains main body portion 22 in position. The distal portions 46 of flaps 24 are folded around the elasticized side edges 18 of the panty. The flap adhesive portions 76 secure the flaps 24 to the underside of the panty.

The sanitary napkin of the present invention is believed to provide a number of benefits over prior sanitary napkins. In prior sanitary napkins, when the flaps are folded down around the curved edges 18 of the crotch portion 12 of the panty, stresses developed in the flaps, particularly in the corner regions of the same. These stresses are magnified when the flaps are attached to the panty's underside. The stresses are further magnified when the panty is pulled up into position and the elastics in the panty edges 18 force the folded portions of the flaps into the uppermost part of the wearer's crotch and thigh. The stresses are most highly concentrated along the fold 19 where the flap 24 changes from being disposed on the body side of the panty to being located on the underside of the panty. In other words, the stresses are concentrated at the edges 18 of the crotch portion 12 of the panty 10. The stresses in the flaps 24 generally follow the arc formed by the edges 18 of the crotch portion 12. These stresses may cause the corner regions of the flaps 24 to bunch longitudinally inward. This reduces the area of the wearer's undergarments the flaps are able to cover. If the stresses are great enough, the flaps 24 can become detached from the panty and the flaps 24 will be less than optimally effective.

In order to eliminate, or at least reduce these stresses, the sanitary napkin 20 is provided with the expandable portions 56 and zones of differential extensibility 70. The expandable portions 56 and zones of differential extensibility 70 preferably reduce the stresses along the fold 19 to such a degree that the flaps 24 will remain attached to the underside of the panty and will not lose their ability to cover a given area of the wearer's undergarments.

The sanitary napkin of the present invention provides a number of advantages over a sanitary napkin provided with a single type of zone of differential extensibility, such as either ring rolled regions or pleated regions. The gathering inward of portions of the sanitary napkin, as noted above, allows the sanitary napkin to additionally expand transversely to fit around the elasticized side edges of the wearer's panty crotch to further reduce stresses on the flaps 24.

Providing the sanitary napkin with expandable portions 56 can also be used to overcome potential design limitations that can occur when attempting to achieve optional amounts of extensibility using only ring rolled zones of differential extensibility. In order to provide the optimal fit around the wearer's panties, it has been found to be necessary to build a relatively large amount of extensibility into such ring rolled regions (preferably about 26 mm in each zone of differential extensibility). The extensibility is particularly important in the region between the narrowest part of the panty crotch and the place where the elasticized edges 18 of the wearer's panties cross the distal edges 46 of the flaps. The flaps 24 need to expand transversely an amount equal to the distance D in FIG. 5 in order to fit smoothly around the curved side edges 18 of the wearer's panties.

There are potentially inherent limitations on the amount of extensibility that can be added to a material by ring rolling the material. These limitations are due to the properties of the material as well as the ring rolling process. The materials generally used in sanitary napkin flaps typically have to be relatively low cost and readily available. Thus, the materials have to be cost-effective for use on disposable absorbent articles. When these materials are ring rolled, any attempt to deform the material in order to impart greater amounts of extensibility to such materials may run the risk of rupturing or creating holes in the material.

One way previously used to achieve the necessary amount of extensibility was to form the flaps 24 as separate elements and then to attach the flaps 24 to the main body portion 22 laterally inward of the longitudinal edges 26 of the main body portion 22. This way allowed the ring rolled regions to start underneath the absorbent core 42. Starting the ring rolling underneath the absorbent core 42 is necessary because it is generally difficult to achieve the desired extensibility by ring rolling the main body portion 22 of the sanitary napkin through the topsheet, backsheet, and core. Forming the flaps 24 from separate elements also allowed greater flexibility in the types of materials that could be used for the flaps (i.e., the flaps would not be limited to the material used in the topsheet 38 and backsheet 40). However, attaching separate flap elements to the main body portion had the disadvantage that it complicated the process of making the sanitary napkin because of the need to make, handle, and attach separate pieces of material to the main body portion of the sanitary napkin.

The structure of the present invention, however, solves these problems, and allows a sanitary napkin having integrally-formed flaps to be made with an optimal amount of extensibility. The structure described herein also allows the optimal amount of extensibility to be achieved with a broader range of materials without encountering the aforementioned material and processing limitations. The gathering of the flaps of the present invention further effectively doubles the amount of flap material that can be ring rolled, if desired, for additional extensibility. The ring rolling is shown, for instance, as extending into the expandable portion 56 of the flap (so that the zone of differential extensibility and expandable portion overlap), in the lower right hand corner of FIG. 1. In addition, since the structure of the sanitary napkin of the present invention does allow the flaps to be provided with such greater amounts of extensibility, it is possible to effectively make flaps which are even longer (measured in the longitudinal direction). This allows the flaps to cover a larger portion of the wearers panty elastics, and to preferably cover a length of the panty elastics that runs substantially the entire length of the main body portion The present invention also provides the sanitary napkin with a lap structure which has advantages over a flap which is pleated and restrained only in the area of the flap transverse centerline $T_1$. One advantage over such a structure is that the restraining of the flaps over a larger distance reduces the tendency of the flaps to become sloppy and unwieldy where they are not restrained. Thus, more efficient use is made of the flap material. In addition, the unrestrained flap material can be positioned more closely along the wearer's panty elastics where it is needed to cover and protect the same from soiling.

The gathered portions can, as described above, also provide double-wall barriers to the flow of bodily exudates in the transverse direction across the body surface 20A of the sanitary napkin 20. In addition, the underside of the double-walled barriers 68 can form tunnel-like structures that can fit over the elastics on the edges 18 of the wearer's panties to further aid in holding the sanitary napkin 20 in proper position during wear. This is especially true for the expandable portions 56 at the ends of the flaps 24.

The sanitary napkin of the present invention is also capable of being made conveniently on a manufacturing line. One non-limiting way of making such a sanitary napkin is to first assembly the components for the sanitary napkin into a pre-formed sanitary napkin that looks very much like the sanitary napkin shown in FIG. 1 would look with the restraints 66 pulled out and the flaps 24 extended. The ring rolling is then added to the corner regions 62 of the sanitary napkin to provide the zones of differential extensibility 70. Following the ring rolling step, the pre-formed sanitary napkin is passed through a folding means, such as folding boards to form the folded sections 60. The restraints 66 are then added to hold the folded sections in place, the adhesive fasteners are applied, and then the releasable wrapper 78 is placed on top of the adhesive fasteners.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A sanitary napkin having a releasable wrapper joined thereto, said sanitary napkin comprising:

a main body portion having a pair of longitudinal side edges, said main body portion comprising a liquid pervious body-facing side, a liquid impervious garment-facing side, an absorbent core positioned between said body-facing side and said garment-facing side, and an adhesive fastener on said garment-facing side of said main body portion, said sanitary napkin further comprising a pair of side flaps extending laterally outward beyond the longitudinal side edges of said main body portion, said flaps each having an adhesive fastener on their garment-facing side;

a releasable wrapper comprising a main wrapping sheet having an inside surface, an outside surface, and a releasable material on said inside surface for releasably securing said main wrapping sheet to said adhesive fastener on said garment-facing side of said main body portion; and at least one flap release element having an inside surface, an outside surface, free ends, and a releasable material on said inside surface for releasably securing said flap release element to one of said adhesive fasteners on said sanitary napkin flaps, said flap release element being pivotably joined to said main wrapping sheet wherein said flap with said flap release element releasably attached thereto is folded over said body-facing side of said sanitary napkin and the free ends of said flap release element overlie the body-facing side of said sanitary napkin while said main wrapping sheet is in a substantially planar configuration.

2. The sanitary napkin of claim 1 wherein said at least one flap release element comprises a single element having two free ends and a portion adjacent to each free end that is capable of being releasably secured to one of said adhesive fasteners on said sanitary napkin flaps.

3. The sanitary napkin of claim 1 wherein said at least one flap release element comprises two elements, each of which is pivotally joined to said main wrapping sheet.

4. The sanitary napkin of claim 1 wherein said main wrapping sheet has a pair of longitudinal side edges and said at least one flap release element is pivotally joined to said main wrapping sheet inboard of the longitudinal side edges of said main wrapping sheet.

5. The sanitary napkin of claim 1 wherein the sanitary napkin and main wrapping sheet are folded together as a unit about two or more transverse axes to form an individual package for the sanitary napkin.

6. The sanitary napkin of claim 5 wherein the folded configuration of the sanitary napkin and main wrapping sheet maintains said flaps in position over the body-facing side of said sanitary napkin.

7. A releasable wrapper for an absorbent article that has a main body portion and side flaps extending laterally outward from the main body portion, and an adhesive fastener on the garment-facing side of its main body portion and on the garment-facing side of its side flaps, said releasable wrapper comprising:

a main wrapping sheet having an inside surface, an outside surface, and a releasable material on said inside surface for releasably securing said main wrapping sheet to the adhesive fastener on the garment-facing side of the main body portion of the absorbent article; and at least one flap release element having an inside surface, an outside surface, and a releasable material on said inside surface for releasably securing said flap release element to one of the adhesive fasteners on the flaps of the absorbent article, said flap release element being pivotably joined to the inside surface of said main wrapping sheet wherein said flap release element is folded over said body-facing side of the absorbent article when an absorbent article is placed on said main wrapping sheet.

8. The releasable wrapper of claim 7 wherein said main wrapping sheet has a pair of longitudinal side edges, and said at least one flap release element is pivotably joined to the inside surface of said main wrapping sheet inboard of the longitudinal side edges of said main wrapping sheet.

* * * * *

UNITED STATES PATENT AND TRADEMARK OFFICE
CERTIFICATE OF CORRECTION

PATENT NO. : 6,383,169 B1 Page 1 of 1
DATED : May 7, 2002
INVENTOR(S) : Sue A. Mills et al.

It is certified that error appears in the above-identified patent and that said Letters Patent is hereby corrected as shown below:

Column 16,
Line 10, after "folded together" please insert -- in a folded configuration --.

Signed and Sealed this

Twenty-third Day of August, 2005

JON W. DUDAS
*Director of the United States Patent and Trademark Office*